US012751621B2

(12) United States Patent
Bertocci et al.

(10) Patent No.: US 12,751,621 B2
(45) Date of Patent: Oct. 6, 2026

(54) SYSTEM FOR THE DETECTION AND ACQUISITION OF PHYSIOLOGICAL AND MOTOR PARAMETERS THROUGH WEARABLE SENSORS

(71) Applicants: SCHEMA31 S.P.A., Rome (IT); MHEALTH TECHNOLOGIES S.r.l., Bologna (IT)

(72) Inventors: Paolo Bertocci, Rome (IT); Luigi Campigli, Fucecchio (IT); Salvatore Manzi, Rome (IT); Sabato Mellone, Bologna (IT); Luca Palmerini, Bologna (IT); Roberta Piccinini, Bologna (IT); Nicola Sgambelluri, Frazione S. Anna (IT); Carlo Tacconi, Bologna (IT); Mario Tesconi, Frazione S. Anna (IT); Fabrizio Zaccheo, Rome (IT); Giuseppe Zupone, Frazione S. Anna (IT)

(73) Assignees: SCHEMA31 S.P.A., Rome (IT); MHEALTH TECHNOLOGIES S.r.l., Bologna (IT)

( * ) Notice: Subject to any disclaimer, the term of this patent is extended or adjusted under 35 U.S.C. 154(b) by 525 days.

(21) Appl. No.: 17/925,351

(22) PCT Filed: May 14, 2021

(86) PCT No.: PCT/IB2021/054156

§ 371 (c)(1),
(2) Date: Nov. 15, 2022

(87) PCT Pub. No.: WO2021/229529

PCT Pub. Date: Nov. 18, 2021

(65) Prior Publication Data

US 2023/0190101 A1 Jun. 22, 2023

(30) Foreign Application Priority Data

May 15, 2020 (IT) ........................ 102020000011218

(51) Int. Cl.
*A61B 5/00* (2006.01)
*A61B 5/0205* (2006.01)
*A61B 5/103* (2006.01)

(52) U.S. Cl.
CPC .......... *A61B 5/0024* (2013.01); *A61B 5/0205* (2013.01); *A61B 5/1038* (2013.01)

(58) Field of Classification Search
CPC ............................ A61B 5/0024; A61B 5/0205
See application file for complete search history.

(56) References Cited

U.S. PATENT DOCUMENTS 10,282,914 B1 * 5/2019 Tran ..................... A61B 5/1128
2012/0116548 A1 * 5/2012 Goree .................. A61B 5/7253
700/90

(Continued)

FOREIGN PATENT DOCUMENTS

WO WO 2017140333 A1 8/2017
WO WO 2019077454 A1 4/2019
WO WO-2020072098 A1 * 4/2020 ......... A61B 5/02444

*Primary Examiner* — Amanda L Steinberg
*Assistant Examiner* — Laura Hodge
(74) *Attorney, Agent, or Firm* — ASLAN LAW, P.C.

(57) ABSTRACT

A system comprising at least one inertial motion sensor, an integrated circuit including an antenna to enable radio communication with other devices; at least one wearable physiological signal detector, an integrated circuit including an antenna to enable radio communication with other devices, capable of detecting/transmitting at least one heart rate datum of the wearer; at least one remote data collection unit capable of communicating with the motion sensor and the physiological parameter detector, of securely storing and processing the data transmitted to it by the latter; at least one (Continued)

operator interface, connected via radio to the motion sensor, to the physiological parameter detector and to the remote data collection unit; synchronization device/unit/component or the like for synchronizing the signals transmitted and received by the different elements; wherein at least one inertial motion sensor comprises connection device/unit/component or the like for the connection to a respective footwear of a patient.

19 Claims, 3 Drawing Sheets

(56) References Cited

U.S. PATENT DOCUMENTS

| | | | | |
|---|---|---|---|---|
| 2013/0128022 | A1* | 5/2013 | Bose | G06Q 10/0833<br>348/77 |
| 2013/0171599 | A1 | 7/2013 | Bleich et al. | |
| 2015/0359457 | A1* | 12/2015 | Blumenthal | A63F 13/218<br>73/172 |
| 2018/0168458 | A1* | 6/2018 | Pekander | A61B 5/086 |
| 2020/0237264 | A1* | 7/2020 | Kimura | G16H 40/63 |

* cited by examiner

SYSTEM FOR THE DETECTION AND ACQUISITION OF PHYSIOLOGICAL AND MOTOR PARAMETERS THROUGH WEARABLE SENSORS

CROSS-REFERENCE TO RELATED APPLICATIONS

This application claims priority to IT patent application No. 102020000011218 filed on May 15, 2020, and this application claims priority to and is a 371 of international PCT Application No. PCT/IB2021/054156 filed on May 14, 2021, the entire contents of which are hereby incorporated by reference.

TECHNICAL FIELD

The present invention belongs to the field of medical systems and, in particular, to the field of systems aimed at detecting and acquiring from patients some of their physiological parameters.

In more detail, the present invention allows both assessing the patients' functional capacity and monitoring their cardiac activity in the light of the motor activity carried out by the patient during the detection.

BACKGROUND ART

Systems for the acquisition of various physiological parameters of patients, both of the temporary and time-consuming type, have long been known.

In the latter case, at the time of interpretation of the data by the medical staff, it is important to know what activities the patient was performing during the acquisition of the physiological parameters.

The main parameters of interest are the assessment of heart rate, oxygen saturation (SpO2) and blood pressure.

The measurements aimed at monitoring the motor activity can take place during standardized tests, such as e.g. while the patient performs certain exercises of preset duration, and is connected to special detection instruments.

Systems are also known which allow the patient's physiological parameters to be acquired over a long period of time, while the patient normally lives outside a hospital or outpatient clinic.

Some wearable sensor solutions have been developed for various purposes, for example to prevent sudden infant death syndrome (WO2019077454), or to monitor the physiological parameters of the patients undergoing treatment and generate alarms in case of their worsening (WO2017140333).

However, the analysis of the measured physiological parameters is often difficult to interpret in the case of patients who are not bedridden or not constantly at rest.

These measurements can occur while the patient is performing activities of any kind, such as running, climbing stairs, or while the patient is standing still.

The information thus collected makes it possible to verify cardiac activity during motor activity and also the peak values at moments of maximum intensity.

In addition, during post-activity rest periods, it becomes possible to check the cardiac recovery progress at preset time intervals.

Therefore, the problem of being able to have a monitoring that allows mapping the motor/cardiac capacity of the person while detecting the type, intensity and duration of the effort.

The information thus collected is important in allowing the clinical operator to identify any factors of risk and define appropriate corrective or maintenance actions.

Depending on the circumstances and severity, the clinical operator may be medical staff, nurses or caregivers.

DESCRIPTION OF THE INVENTION

The problem is therefore felt of having a system capable of detecting and acquiring the physiological parameters of the patient that, at the same time, is able to detect and acquire the data relating to the motor activity developed instant by instant during monitoring.

The need is also felt to have a system that allows the storage of the collected data, both physiological and related to the motor activity and make the same data available for clinical use.

In particular, the walking parameters to be parameterized are the speed of the walk and how this speed varies over time, the rhythm, the amplitude and duration of the stride, the greater or lesser symmetry of the body during the walk, the distance covered, and the like.

Based on the detection of the aforementioned parameters it is required to be able to assess the metabolic equivalent of the effort made by the patient and the energy consumed.

The main physiological parameters of interest are heart rate, body temperature, oxygen saturation, respiration rate, the electrocardiographic signal of each lead, and the signal related to the person's breathing.

The need is also felt to be able to customize the measured data in order to create subsets of parameters to be used and associated at will to the different subjects being tested.

A further object of the present invention is to provide a system that is easily customizable by the clinical operator depending on specific risk factors of the individual patients and that can be progressively updated and modified.

Another object of the present invention is to provide a system that allows managing the motor and physiological parameters of multiple patients and that allows the medical staff and patients to interact with each other in a simple, convenient and fast manner.

The solution to the drawbacks summarized above and others that are obvious to the expert in the field is provided by a medical system comprising the following elements, each of which comprises both hardware components and software modules.

- At least one inertial motion sensor, comprising means to connect it to a respective patient's footwear, a radio transmitter and a power source, with a software module for extracting data about the patient's walking movements and their transmission by radio waves.
- At least one detector of physiological parameters which is wearable by the patient, interfaced via radio with said at least one motion sensor; the parameters to be detected are those of cardiac and respiratory activity, in addition to body temperature. Excellent results are obtained with a system of electrode pads to be applied to the patient's chest, or with a finger pulse oximeter or even with a wrist cuff.
- At least one remote data collection unit, interfaced via radio both with said at least one motion sensor and with said at least one physiological parameter detector; typically this is a data center that may reside on a remote computer or in a cloud.
- At least one operator interface, such as e.g. a computer or smart phone, interfaced via radio with each of the previous three elements independently.

According to a particularly comprehensive solution, the inertial motion sensor is functionally coupled to at least one plantar pressure sensor; depending on the identified embodiment the latter may share the power source and the radio transmitter of the inertial motion sensor, or it may comprise its own radio transmitter and its own power source.

The software module of the two sensors can also be shared or independent.

The software modules of the different elements provide mutual synchronization by periodically exchanging messages.

Specifically, synchronization messages are exchanged between the right and left footwear and between both footwear and the physiological parameter detector. Synchronization can occur in several manners of known type. For example, each synchronization message may comprise a piece of information selected from the acquisition timestamp of the signal samples, the Universal Coordinated Time, if this function is included in the system, or the progressive number of the synchronization messages sent; it is worth to specify that the synchronization message can contain any information useful for the intended purpose.

Also the frequency of sending synchronization messages can vary and can be set, for example, every minute. Synchronization can take place via wireless connection (via Bluetooth, WiFi or the like); the synchronization that will be obtained can be estimated in a maximum window of 10-30 milliseconds and is considered sufficient.

The sending of the message will have a settable periodicity. For example, you can set it to every minute.

For each synchronization message received, a marker will be added to the log file of the data collected by the receiver's sensors. For each synchronization message sent, a marker will be added to the sender's log file.

EMBODIMENTS OF THE INVENTION

Figure 1:
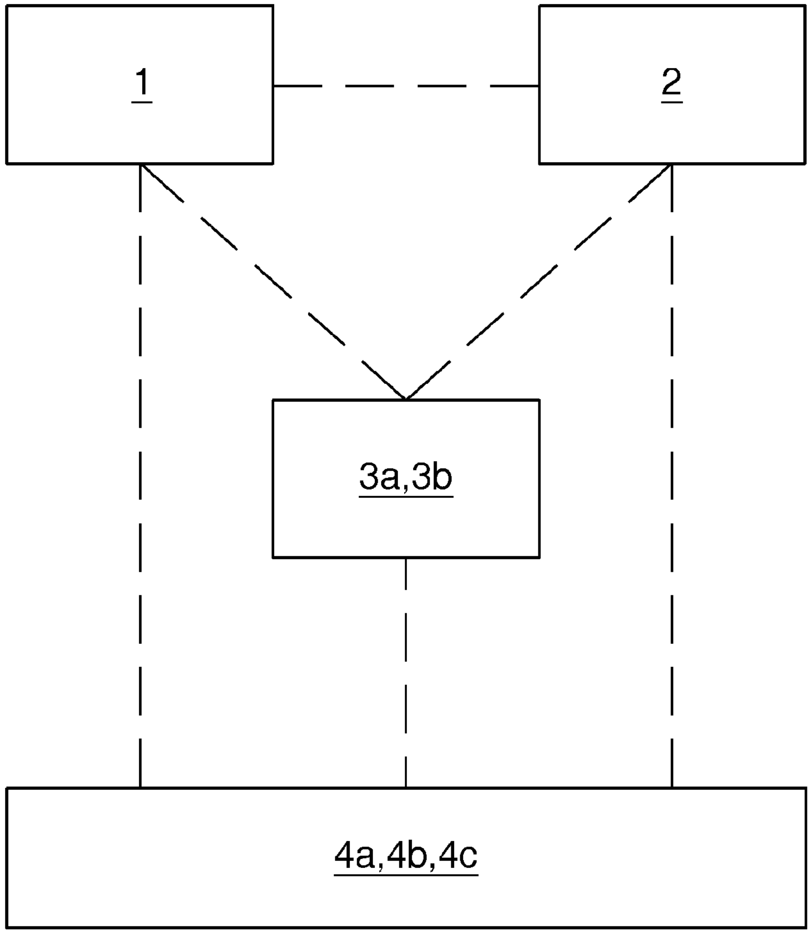
FIG. 1 shows a diagram of the system, where the inertial motion sensor (1), the physiological parameter detector (2), the remote data collection unit (3*a*, 3*b*) and the operator interface (4*a*, 4*b*, 4*c*) are indicated.
Figure 2:
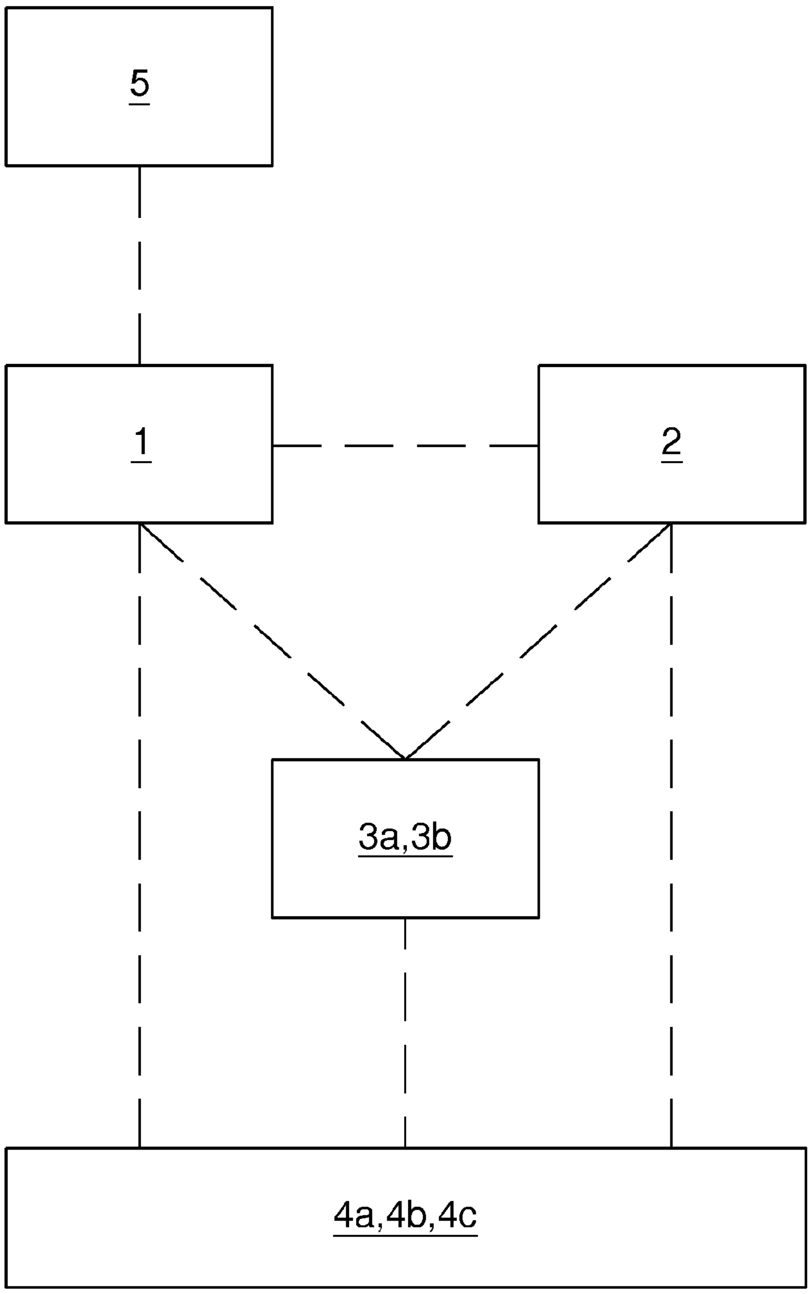
FIG. 2 shows a diagram of the system in an embodiment that also comprises a plantar pressure sensor (5).
Figure 3:
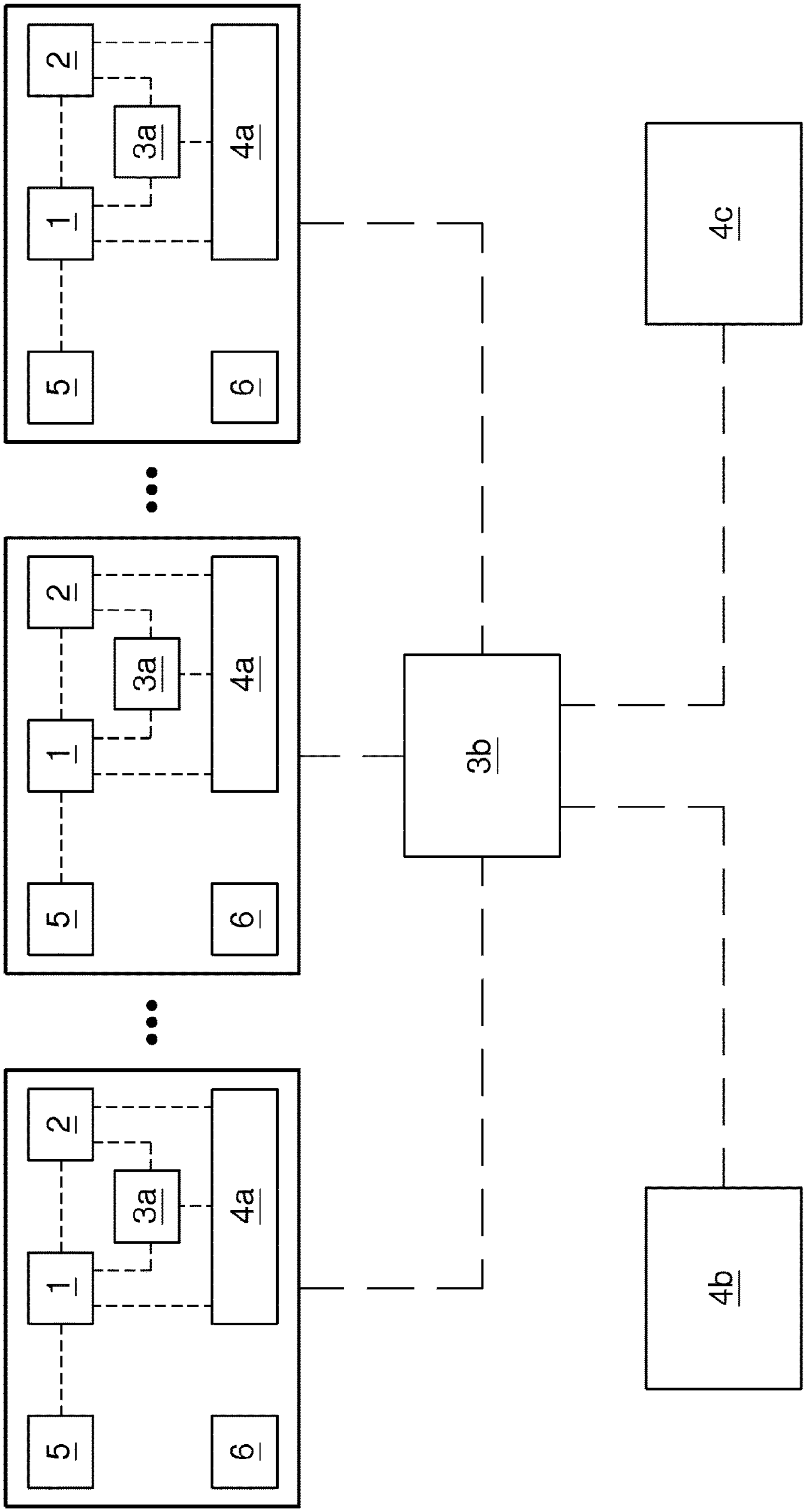
FIG. 3 shows a diagram of the system in an embodiment comprising a plurality of inertial motion sensors (1), a plurality of physiological parameter detectors (2).

In a simple and practical embodiment, the present invention comprises two inertial motion sensors (1), each of which is respectively connected to one of the patient's footwear by methods of attachment of known type which, by way of example, may include external casings to be attached to the footwear, or in the upper of the footwear, or by permanent insertion into the sole, insole or foot bed of each footwear.

Advantageously, the inertial motion sensor (1) samples the sensed data with a sampling rate greater than 50 Hz.

Preferably, the inertial motion sensor (1) samples the sensed data with a sampling rate selected from 50 Hz, 100 Hz, 200 Hz.

As discussed above, each inertial motion sensor can be coupled to a respective plantar pressure sensor (5) and the two sensors may also be integrated into a single device.

Advantageously, the plantar pressure sensor (5) also samples the sensed data with a sampling rate greater than 50 Hz.

Preferably, the plantar pressure sensor (5) samples the sensed data with a sampling rate selected from 50 Hz, 100 Hz, 200 Hz.

The inertial motion sensor (1) may contain accelerometers, gyroscopes and magnetometers and shall contain at least one mono-axial accelerometer or at least one mono-axial gyroscope or at least one mono-axial magnetometer.

Conveniently, the position of the plantar pressure sensor (5) inside the footwear is selected according to the type of information you want to extract. For example, if you want to extract information about the support of the back of the foot, it will be useful to place the plantar pressure sensor in the heel area of the footwear.

According to a convenient and practical embodiment, the physiological parameter detector (2) may comprise an adhesive device to be applied to the chest of the patient comprising at least one sensor capable of detecting the heartbeat of the patient, functionally connected to at least one electronic board comprising:

- the circuits required for protection against defibrillation;
- a push-button, or alternative means, for switching on;
- an integrated circuit including an antenna to allow the communication with other elements;
- one or more batteries to ensure power supply;
- a transducer of physiological signals (sensing unit) comprising at least 2 ECG (electrocardiogram) channels, at least 4*a*, 4*b*, 4*c* sensing electrodes, at least one patient body temperature sensing sensor, and one oxygen saturation sensing sensor.

Within the same inventive concept, it is also possible to have a different embodiment wherein the physiological parameter detector (2) comprises a finger pulse oximeter of the hand, capable of acquiring at least the heartbeat of the patient, by means of at least one sensor positioned on a finger. Also in this case, the physiological parameter detector (2) is functionally connected to at least one electronic board comprising:

- a push-button, or alternative means, for switching on;
- an integrated circuit including an antenna to allow communication with other elements;
- one or more batteries to ensure power supply;
- a transducer of physiological signals (sensing unit) comprising at least one optical sensor.

A further embodiment provides that the physiological parameter detector (2) comprises a wrist bracelet capable of acquiring at least the heart beat through at least one sensor positioned between the bracelet and the wrist; also in this case the detector is functionally connected to an electronic board capable of performing the same functions exposed in the previously described embodiments.

A particularly complete and high-performing embodiment requires that the physiological parameter detector (2) also comprises a memory circuit to store ECG signals, the parameters of the patient's oxygen saturation (SpO2) and of body temperature.

Particularly high-performing electronic boards comprise circuits that can be programmed by commands received via radio and/or other circuits capable of sending information about the status of the detector itself.

Electronic devices have also been developed whereby the physiological parameter detector (2) is capable of processing the signals emitted by the transducers, such as e.g. ECG signal, oxygen saturation (SpO2), and the temperature signal to provide a subset of physiological parameters.

The inertial motion sensor (1) and the physiological parameter detector (2) exchange information via radio both with each other and with the remote data collection unit (3*a*, 3*b*) and with the operator interface (4*a*, 4*b*, 4*c*); the latter also exchange information directly with each other, again via radio.

The remote data collection unit (3*a*, 3*b*) is configured to store information/data in files and/or databases, thus defining a distributed and/or centralized, highly efficient and secure information technology infrastructure in compliance with the reference regulations of the relevant territory. In summary, the remote data collection unit (3*a*, 3*b*) is configured to perform at least one of the following functions:

- communicate with the motion sensor (1), with the physiological parameter detector (2), and with the operator interface (4*a*, 4*b*, 4*c*) to receive and provide the required data and information;
- store the data transmitted to it by both the inertial motion sensor (1) and the physiological parameter detector (2);
- maintain the levels of security for the collected data, by complying with the industry standards, such as e.g. HIPAA (Health Insurance Portability and Accountability Act) and HITRUST;
- process the data coming from both the inertial motion sensor (1) and the physiological parameter detector (2) to generate information required both in the motor and physiological domains, where appropriate, by combining these with each other based on the requests made by the clinical staff via the operator interface (4*a*, 4*b*, 4*c*).

The data processing and the extraction procedure of the motor parameters usually comprise the following steps:

a. Conditioning of inertial (accelerometer and/or gyroscope) signals at input.

b. Extraction of notable points, including:
   - Heel Strike
   - Foot Flat
   - Mid-Stance
   - Heel-Off
   - Toe-Off
   - Mid-Swing c. Generation of walking and motion parameters based on the notable points.

In this regard, it should be noted that the extraction procedure for extracting the notable points can be appropriately varied for each placement of the inertial motion sensor (1).

The basic data extraction procedure will be carried out for each positioning of the inertial motion sensor (1) and if said procedure fails to correctly identify the notable points, the procedure will be refined until such notable points are correctly positioned in the acquired signal.

Depending on the processing capacity of the physiological parameter detector (2), the physiological parameters can be directly calculated by the detector and then stored in the remote data collection unit (3*a*, 3*b*) which will then start the data analysis by processing the signals with algorithms aimed at extracting a subset or all the physiological parameters of specific interest. If the physiological parameter detector (2) communicates all the parameters of interest, or a subset of them, processing will not be started for these parameters. Finally, if required, a procedure useful to generate the factors of risk will be initiated and the parameters and information on the subject's factors of risk will be made available to clinical staff via the operator interface (4*a*, 4*b*, 4*c*). The latter element interfaces with the inertial motion sensor (1), the physiological parameter detector (2) and the remote data collection unit (3*a*, 3*b*) and makes the information available to the clinical operator, also allowing him/her to interact with the system, possibly after authentication of the clinical operator.

The collection and sending of data from the inertial motion sensor (1) and from the physiological parameter detector (2) can take place at different time intervals, depending on the specific features of the case.

As further elaborated later in the text, prior registration of the clinical operator may also be provided, the prior registration may ensure different levels of interaction with the system of the present invention differentiating, for example, between physicians, nurses/caregivers and the patient himself.

As an example, it is reported that the medical staff accesses the system via the operator interface (4*a*, 4*b*, 4*c*), which is configured to carry out at least one of the following operations:

- observe the specific characteristics linked to the parameters generated by the system in order to implement corrective or conservative actions for the patient/user's state of health, for example, if the speed of the patient's walk detected by the system is deemed unsuitable by the doctor, the doctor may suggest corrective actions;
- take note of any risk data generated by the system for each patient who has been previously associated with it;
- set risk data in the system;
- set the list of calculable parameters to be included in the reports;
- set the list of parameters that defines a new risk datum;
- set the threshold value for each parameter in the list that defines a new risk datum;
- set the rule that defines a new risk datum;
- suggest corrective or maintenance actions to the user patient based on the information provided by the system;
- indicate to the patient how to use the inertial motion sensor (1) and the physiological parameter detector (2), such as e.g. when to start and stop wearing them, how long to wear them and any activities to be carried out while wearing them;
- check, by means of the parameters calculated by the system, whether the corrective or maintenance actions suggested by him have been implemented and/or whether they have had the expected effects;
- receive feedback from the patient/user, caregiver, family member;
- connect to the inertial motion sensor (1) and/or to the physiological parameter detector (2), setting them on the basis of specific needs, selecting these from a set of possible settings available;
- receive data collected by the inertial motion sensor (1) and/or by the physiological parameter detector (2);
- perform the instrumentation of the functional test, i.e. obtain objective data supporting the diagnosis; through this application the doctor will be able to start and stop the data acquisition during the period of the test only and ask the system to calculate the parameters and risk data related only to the period of the test so that the system will collect the data listed above and process them in order to obtain the required information.

In particular, the inertial motion sensor (1) is configured to detect at least one motor datum of the patient wearing it.

By motor datum is meant any data detectable by means of at least one mono-axial accelerometer and/or one mono-axial gyroscope and/or one mono-axial magnetometer.

On the other hand, the wearable physiological signal detector (2) is configured to detect at least one physiological datum of the patient wearing it.

By physiological datum is meant heart rate, body temperature, oxygen saturation, respiration rate, electrocardiographic signal from each lead, and the person's breathing signal.

Advantageously, the remote data collection unit (3*a*, 3*b*) is configured to process at least one of the following data depending on at least one of either the motor datum or the physiological datum:

- at least one risk datum defining the risk of a patient of experiencing a motion and/or physiologic complication;
- at least one characteristic datum of the walk of at least one patient;
- at least one characteristic datum of the metabolism of at least one patient.

Further embodiments of the invention cannot however be ruled out in which the inertial motion sensor (1) is configured to process and/or store the characteristic datum of the walk and/or the characteristic datum of the metabolism of at least one patient.

Further embodiments of the invention cannot also be ruled out wherein the wearable physiological signal detector (2) is configured to process and/or store the characteristic datum of the walk and/or the characteristic datum of the metabolism of at least one patient.

According to the invention, the characteristic datum of the walk is preferably selected from the list comprising: walking speed, walking speed variability, walking rhythm, walking asymmetry, walking variability, stride length of the right and/or left footwear, stride duration of the right and/or left footwear, pitch contact of the right and/or left footwear, pitch cycle of the right and/or left footwear, distance traveled and number of steps taken by the right and/or left footwear.

The term pitch cycle of the right and/or left footwear is used to indicate swing phase, single support, double support.

Advantageously, the remote data collection unit (3*a*, 3*b*) is configured to process a plurality of characteristic data of the walk.

In this way, the system is configured to provide a complete gait analysis of the patient.

Similarly, the remote data collection unit (3*a*, 3*b*) is configured to process a plurality of characteristic data of the metabolism.

This solution allows the system to provide for a complete picture of the patient's motion/metabolic activity, e.g., by means of a few descriptive periods of the patient's activity defined by at least the characteristic data of the metabolism and/or any combination thereof.

These descriptive periods are selected from: lying down, sedentary, active, walking.

Preferably, the characteristic datum of the metabolism is selected from the list comprising: actigraphy, MET (Metabolic Equivalent) and Energy Expenditure.

Advantageously, the operator interface (4*a*, 4*b*, 4*c*) is configured to allow a user to:

- display the data transmitted by the inertial motion sensors (1) and/or by the wearable physiological signal detectors (2); and/or
- display at least one indicative datum of a corrective action to be performed by at least one patient; and/or
- display the data stored and/or processed by the remote data collection unit (3*a*, 3*b*);
- display at least one risk datum.

Conveniently, the system comprises a plurality of inertial motion sensors (1), each connectable to the footwear of a respective patient, and a plurality of wearable physiological signal detectors (2), each wearable by a respective patient.

Furthermore, advantageously, the remote data collection unit (3*a*, 3*b*) comprises at least one of:

- a plurality of distributed units (3*a*), each configured to store and process the data transmitted to it by the motion sensor (1) and by the physiological parameter detector (2) worn by a corresponding patient;
- at least one centralized unit (3*b*) configured to store and process the data transmitted to it by the motion sensors (1) and by the physiological parameter detectors (2) worn by a plurality of patients.

Advantageously, in the case where the remote data collection unit (3*a*, 3*b*) comprises both the distributed units (3*a*) and the centralized unit (3*b*), the same are configured to share data with each other.

Preferably, the distributed unit (3*a*) is of the type of a charging device (6) of the inertial motion sensor (1).

Further embodiments of the invention cannot however be ruled out wherein the distributed unit (3*a*) coincides with the inertial motion sensor (1).

Preferably, the centralized unit (3*b*) is of the type of a cloud server.

Advantageously, the operator interface (4*a*, 4*b*, 4*c*) comprises at least one of:

- at least one patient interface (4*a*) that can be used by a corresponding patient to display the data relating to the patient;
- at least one caregiver interface (4*b*) that can be used by a caregiver to display the data relating to one or more patients;
- at least one doctor interface (4*c*) that can be used by a doctor to:
- indicate the indicative datum of a corrective action to be carried out by at least one patient; and/or
- indicate/define at least one risk datum.

By the words "data relating to a patient" is meant:

- the data detected by the inertial motion sensor (1) and/or by the physiological parameter detector (2) worn by the patient; and/or
- the data derived/processed from the data detected by the inertial motion sensor (1) and/or by the physiological parameter detector (2); and/or
- the data concerning one or more of the data detected by the inertial motion sensor (1) and/or by the physiological parameter detector (2) worn by the patient; and/or
- the data concerning such derived/processed data.

Advantageously, the operator interface (4*a* 4*b*, 4*c*) comprises a plurality of patient interfaces (4*a*), each for each patient to be monitored.

Similarly, the operator interface (4*a* 4*b*, 4*c*) comprises a plurality of caregiver interfaces (4*b*) and/or doctor interfaces (4*c*), each for each caregiver/doctor and/or group of caregivers/doctors.

The described system allows motion and physiological data to be detected from multiple patients and to have them processed in a centralized and/or distributed manner.

In particular, this system allows the medical staff to monitor the health status of multiple patients and interact with them in a timely and selective manner.

Similarly, the system allows each patient to monitor their own health status and interact with the medical staff.

The invention claimed is:

1. A system for the acquisition of physiological and motor parameters, said system comprising:

at least one inertial motion sensor, comprising at least one mono-axial accelerometer and/or one mono-axial gyroscope and/or one mono-axial magnetometer, at least one power source and an integrated circuit including at least one antenna to enable radio communication;

at least one wearable physiological parameter detector, comprising the at least one power source and the integrated circuit including the at least one antenna to enable the radio communication, capable of detecting and transmitting at least one heart rate datum of a patient;

at least one remote data collection unit, comprising hardware components and software modules, capable of electronically communicating with said at least one inertial motion sensor and said at least one wearable physiological parameter detector, and of securely storing and processing the data transmitted to the at least one remote data collection unit by said at least one physiological parameter detector and by said at least one inertial motion sensor; and at least one operator interface, connected via radio to said at least one inertial motion sensor, to said at least one physiological parameter detector, and to said at least one remote data collection unit;

wherein said at least one inertial motion sensor comprises connection means for the connection to a respective footwear of the patient;

wherein said at least one inertial motion sensor and said at least one physiological parameter detector exchange information via radio both with each other and with said at least one remote data collection unit and with said at least one operator interface;

wherein said at least one remote data collection unit and said at least one operator interface also exchange information directly with each other, again via radio;

wherein said system further comprises:

a plurality of said inertial motion sensors, each connectable to the footwear of said patient; and a plurality of said wearable physiological parameter detectors, each wearable by said patient;

wherein said at least one remote data collection unit includes one or more of:

a plurality of distributed units, each configured to store and process the data transmitted to said plurality of distributed units by the motion sensor and by the plurality of said wearable physiological parameter detectors worn by said patient; and at least one centralized unit configured to store and process the data transmitted to said at least one centralized unit by the motion sensors and by the plurality of said wearable physiological parameter detectors worn by said patient;

wherein said distributed units and said at least one centralized unit are configured to share data with each other;

wherein:

said at least one inertial motion sensor is configured to detect at least one motor datum of the patient wearing said at least one inertial motion sensor;

said at least one wearable physiological signal parameter is configured to detect at least one physiological datum of the patient wearing said at least one wearable physiological parameter detector; and said remote data collection unit is configured to receive, store, and process at least one of said at least one motor datum and said at least one physiological datum so as to determine at least one risk datum defining the risk of said patient of experiencing a motor and/or physiologic complication depending on at least one of said at least one motor datum and said at least one physiological datum; and wherein the at least one operator interface is configured to carry out at least one of the following operations in cooperation with the at least one remote data collection unit:

set configuration data in the system defining said at least one risk datum;

set a list of parameters that defines said at least one risk datum and that is used by the remote data collection unit to determine said at least one risk datum;

set a threshold value for each parameter in the list that defines said at least one risk datum; and/or set a rule that defines said at least one risk datum for use by the remote data collection unit in determining said at least one risk datum.

2. The system according to claim 1, wherein said at least one inertial motion sensor is functionally associated with a plantar pressure sensor, in turn connected to a footwear of the patient, said plantar sensor comprising the at least one power source, and an integrated circuit including the at least one antenna for radio communication.

3. The system according to claim 2, wherein said at least one wearable physiological parameter detector comprises an adhesive configured to reversibly connect said at least one wearable physiological parameter detector to the chest of the patient and is functionally connected to at least one electronic board consisting of: the circuits adapted to protect against defibrillation, a device for switching on, an integrated circuit including the at least one antenna to allow the communication, at least one battery for power supply, and a transducer of physiological signals including at least 2 electrocardiogram (ECG) channels, at least 3 sensing electrodes, or at least one sensing sensor for the patient's body temperature.

4. The system according to claim 2, wherein said at least one wearable physiological parameter detector comprises at least one sensing sensor of the oxygen saturation.

5. The system according to claim 2, wherein said at least one wearable physiological parameter detector comprises a finger pulse oximeter and is functionally connected to at least one electronic board comprising: a device for switching on, an integrated circuit consisting of the at least one antenna to allow the communication, one or more batteries to ensure power supply, and a transducer of physiological signals having at least one optical sensor.

6. The system according to claim 1, wherein:

said wearable physiological parameter detector comprises an adhesive configured to reversibly connect said wearable physiological parameter detector to the chest of the patient;

the wearable physiological parameter detector is functionally connected to at least one electronic board having one or more of:

the circuits necessary for protection against defibrillation, a device for switching on, an integrated circuit including the at least one antenna to allow the communication, at least one battery for power supply, and a transducer of physiological signals including:

at least 2 electrocardiogram (ECG) channels, at least 3 sensing electrodes, or at least one sensing sensor for the patient's body temperature.

7. The system according to claim 1, wherein said wearable physiological parameter detector comprises at least one sensing sensor of the oxygen saturation.

8. The system according to claim 1, wherein:

said at least one wearable physiological parameter detector comprises a finger pulse oximeter and is functionally connected to said at least one electronic board;

the at least one electronic board comprises one or more of:

a device for switching on, an integrated circuit having the at least one antenna to allow the communication, one or more batteries to ensure power supply, and a transducer of physiological signals having at least one optical sensor.

9. The system according to claim 1, wherein said at least one wearable physiological parameter detector comprises a wrist bracelet and is functionally connected to at least one electronic board comprising:

a device for switching on, an integrated circuit having the at least one antenna to allow the communication, one or more batteries to ensure power supply, and a transducer of physiological signals having at least one sensor of the optical or electrical type.

10. The system according to claim 1, wherein the radio communications are according to wireless communication protocols.

11. The system according to claim 1, wherein said at least one operator interface is a computer, or a smart phone, or a tablet.

12. The system according to claim 1, wherein said at least one inertial motion sensor samples the sensed data with a sampling frequency greater than 50 Hz.

13. The system according to claim 1, wherein said remote data collection unit is configured to process at least one of the following data depending on at least one of said at least one motor datum and said at least one physiological datum:

at least one characteristic datum of the walk of said patient; or at least one characteristic datum of the metabolism of said patient.

14. The system according to claim 13, wherein said at least one characteristic datum of the walk is selected from the list consisting of: walking speed, walking speed variability, walking rhythm, walking asymmetry, walking variability, stride length of the right and/or left footwear, stride duration of the right and/or left footwear, pitch contact of the right and/or left footwear, pitch cycle of the right and/or left footwear, distance traveled, and the number of steps taken by the right and/or left footwear.

15. The system according to claim 13, wherein said at least one characteristic datum of the metabolism is selected from the list consisting of: actigraphy, MET (Metabolic Equivalent), and Energy Expenditure.

16. The system according to claim 1, wherein said at least one operator interface is configured to allow the patient to:

display the data transmitted by the inertial motion sensors and/or by the wearable physiological parameter detectors; and/or display at least one datum indicative of a corrective action to be carried out by said patient; and/or display the data stored and/or processed by said remote data collection unit; and/or display said at least one risk datum.

17. The system according to claim 1, wherein said plurality of distributed units are of the type of a charging device of said at least one inertial motion sensor.

18. The system according to claim 1, wherein said at least one centralized unit is of the type of a cloud server.

19. The system according to claim 1, wherein said at least one operator interface includes:

a patient interface adapted to display the data relating to the patient;

a caregiver interface adapted to display the data relating to said patient; or a doctor interface adapted to:

indicate said at least one datum indicative of a corrective action to be carried out by said patient; and/or indicate/define said at least one risk datum.

* * * * *